(12) United States Patent
Davis et al.

(10) Patent No.: US 6,628,386 B2
(45) Date of Patent: Sep. 30, 2003

(54) PARTICLE DETECTION BEAM (75) Inventors: Clay Davis, Redondo Beach, CA (US); Donald Mead, Carlsbad, CA (US); Gregory Quist, Escondido, CA (US)

(73) Assignee: PointSource Technologies, LLC, Escondido, CA (US)

( * ) Notice: Subject to any disclaimer, the term of this patent is extended or adjusted under 35 U.S.C. 154(b) by 0 days.

(21) Appl. No.: 10/015,428

(22) Filed: Dec. 12, 2001

(65) Prior Publication Data

US 2003/0107734 A1 Jun. 12, 2003

(51) Int. Cl.$^7$ .............................................. G01N 21/00
(52) U.S. Cl. ..................................... 356/338; 356/343
(58) Field of Search ................................ 356/337, 338, 356/340, 341, 342, 343, 335, 336

(56) References Cited

U.S. PATENT DOCUMENTS

| | | |
|---|---|---|
| 3,770,351 A | 11/1973 | Wyatt |
| 3,901,602 A | 8/1975 | Gravatt, Jr. |
| 4,070,113 A | 1/1978 | Frazer et al. |
| 4,173,415 A | 11/1979 | Wyatt |
| 4,265,538 A | 5/1981 | Wertheimer |
| 4,548,500 A | 10/1985 | Wyatt et al. |
| 4,565,448 A | 1/1986 | Abbott et al. |
| 4,680,977 A * | 7/1987 | Conero et al. ............ 73/861.41 |
| 4,728,190 A | 3/1988 | Knollenberg |
| 4,906,094 A | 3/1990 | Ashida |
| 4,942,305 A | 7/1990 | Sommer |
| 4,952,055 A | 8/1990 | Wyatt |
| 4,987,539 A | 1/1991 | Moore et al. |
| 5,125,737 A | 6/1992 | Rodriguez et al. |
| 5,247,340 A | 9/1993 | Ogino |
| 5,414,508 A | 5/1995 | Takahashi et al. |
| 5,436,465 A | 7/1995 | Borden et al. |
| 5,534,999 A | 7/1996 | Koshizuka et al. |
| 5,627,040 A | 5/1997 | Bierre et al. |
| 5,737,078 A | 4/1998 | Takarada et al. |
| 5,861,950 A * | 1/1999 | Knowlton .................... 356/338 |
| 5,999,256 A | 12/1999 | Jones et al. |
| 6,023,324 A | 2/2000 | Myers |
| 6,100,541 A | 8/2000 | Nagle et al. |
| 6,111,642 A * | 8/2000 | DeFreez et al. ............. 356/337 |
| 6,118,531 A | 9/2000 | Hertel et al. |
| 6,120,734 A | 9/2000 | Lackie |
| 6,519,033 B1 * | 2/2003 | Quist et al. .................. 356/337 |

FOREIGN PATENT DOCUMENTS

GB        2 317 228 A     3/1998   .......... G01N/15/14

* cited by examiner

Primary Examiner—Michael P. Stafira
(74) Attorney, Agent, or Firm—Leon D. Rosen (57) ABSTRACT

An apparatus for identifying microscopic particles in a fluid, includes a laser beam (16) that passes though a narrow detect zone (22), and photodetectors (30) that detect light scattered by microscopic particles that pass through the detect zone. The laser beam has a horizontal width (W) that is a plurality of times as great as its average vertical thickness (T), to increase the number of particles passing through the zone while minimizing the time of each particle in the zone. A quadrant detector (48) that is used to detect deviation of the laser beam from a predetermined path, is oriented about 45° from the usual direction. The laser beam is generated by a diode laser (82) whose output passes through two appropriately-positioned cylindrical lenses (84, 86) to produce the desired the ratio of width (W) to thickness (T).

15 Claims, 3 Drawing Sheets

PARTICLE DETECTION BEAM

BACKGROUND OF THE INVENTION

Microscopic particles, and especially pathogens, which lie in a stream of fluid such as air or water, can be detected by scattering of light (from infrared through visible to far ultraviolet, and possibly to soft x-rays). Usually a laser beam is employed as the light source because of its small size and high power density. The narrow laser beam is directed primarily perpendicular to the direction of fluid flow, and a plurality of photodetectors detect light scattered in different directions by a particle as it passes through the laser beam. The pattern of light scattering by an unknown particle can be compared to multiple scattering patterns for each of a plurality of known particles (which are pathogens). When there is a high correlation between the scatter subpattern, or eventvector for the unknown particle and multiple eventvectors for a particular known specie of particle, then this indicates a high probability that the unknown particle is the particular known specie of particle.

In constructing such a particle identifying device, it is important to assure that the laser beam has certain characteristics. It is desirable that only one particle at a time pass through the laser beam for accurate identification. It is also desirable that the period between successive particles passing through the laser beam is short, so that a large number of particles can be detected in a moderate period of time and during the passage of a sample of fluid that contains the particles. It is important that the laser be directed along a predetermined path and that it have a predetermined orientation and polarization. If the beam deviates considerably from the designated path, then photodetectors that pick up scattered radiation from a small detect zone along the path will not properly detect scattered radiation. Proper orientation of the polarized laser beam assures proper detection by photodetectors with polarizing filters and consequent correct identification of the particles.

SUMMARY OF THE INVENTION

In accordance with one embodiment of the present invention, an apparatus is provided for identifying microscopic particles in fluid by detecting scattering of light from particles passing through a detect zone lying along a narrow beam, which decreases the time spent by each particle intraversing the detect zone while increasing the frequency of particles passing through the detect zone. The beam has a width and thickness that are each perpendicular to the direction of the beam. The beam width, which is perpendicular to the direction of fluid and particle flow, is a plurality of times greater than the beam thickness which is parallel to the direction of fluid and particle flow. The small beam thickness results in each particle rapidly passing through the beam to minimize the number of times when two or more particles pass through the beam and data cannot be used. The wide beam width increases the frequency at which particles pass through the beam, to provide more data in a given time period.

The precise direction of the beam is checked in a test wherein the beam strikes a quadrant detector and the outputs of the quadrant detector are delivered to a difference circuit. The quadrant detector is of the type that has four photocells lying in each of four quadrants that are separated by perpendicular lines. In order to better detect the wide but small-thickness beam, the quadrant detector is oriented so the perpendicular lines are each angled about 45° to the horizontal when the beam width direction is horizontal.

An activator is provided for moving the quadrant detector or beam relative to one another, in a direction parallel to the beam width. This enables a determination of the beam width at the quadrant detector. An activator also can move the quadrant detector relative to the beam in a direction parallel to the beam thickness to check the beam thickness.

The beam is generated by a laser diode whose output expands in both vertical and horizontal planes. A first primarily cylindrical convex lens in front of the laser diode, largely collimates the beam in a vertical plane to fix the thickness of the beam. A second primarily cylindrical convex lens which is on a side of a first lens opposite the diode, largely collimates the beam in a horizontal plane to fix the width of the beam. The spacing of the lenses is chosen to produce the desire ratio of width to thickness.

The novel features of the invention are set forth with particularity in the appended claims. The invention will be best understood from the following description when read in conjunction with the accompanying drawings.

DESCRIPTION OF THE PREFERRED EMBODIMENTS

Figures 1, 3:
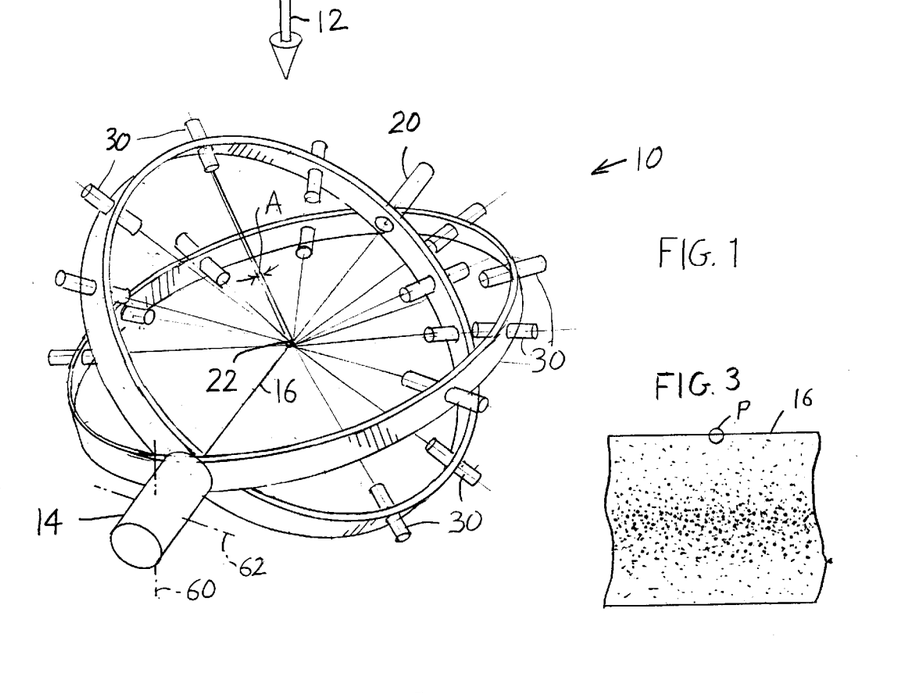
FIG. 1 is an isometric view of one possible apparatus for detecting scattering of light by microscopic particles contained in a fluid.
FIG. 3 is a view of a portion of FIG. 2, showing a particle entering the beam, and indicating the variation in intensity along the thickness of the beam.

FIG. 1 illustrates an apparatus 10 which is intended to detect particles in a fluid stream that moves along the direction of arrow 12. The apparatus includes a laser beam source 14 that generates a narrow laser beam 16 that reaches a dump 20. The dump absorbs almost all of the laser beam power, except for a small amount that is scattered by a particle. When a particle in the fluid stream passes through a detection zone 22 lying along the laser beam, light scatter from that zone is detected by photodetectors 30 spaced about the zone. Sixteen photodetectors are shown in FIG. 1, but there can be more or less. Some experiments suggest that reliable identification may be possible using as few as six photodetectors. Each photodetector has a very narrow detection angle A such as 1.5°, and is spaced by a small distance from the zone, such as 1.5 inches. Accordingly, each detector detects light lying in a square of about 1.5 mm on a side at the detection zone 22.

It would be possible to use a laser beam with a circular cross section. However, a particle passing through most of the diameter of the circular beam would remain in the beam for a considerable period of time. This increases the possibility that another particle would enter the detection zone of the laser beam while the first particle was still present in it, resulting in data that cannot be used.

Figure 2:
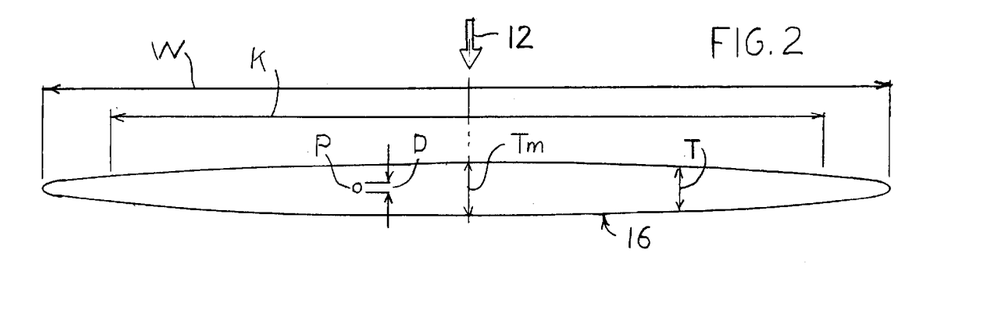
FIG. 2 is an enlarged sectional view of the laser beam produced by the apparatus of FIG. 1, in a detect zone.

In accordance with one feature of the present invention, the laser beam has a cross section such as shown in FIG. 2 for beam 16, with a large width W and small thickness T. The width W is in a direction perpendicular to the direction 12 of fluid flow, while the thickness T is parallel to the direction of fluid flow and is vertical in the figures. In this case, we define the thickness T as the median average thickness (half of the beam is thicker and half is thinner), although another average (mean, mode, etc.) Could be used. The particles such as P to be detected by the apparatus, are all of a diameter less than the thickness T of the beam.

It can be seen in FIG. 1 that the path of the fluid moving along direction 12 is greater than the width of the laser beam 16, especially since the narrow dump 20 absorbs virtually all of the beam that is not scattered. As a result, particles in the fluid stream can pass through any location along the width of the laser beam, including locations at extreme opposite sides of the beam.

FIG. 3 shows a particle P passing through the detection zone of the beam 16. Scattering starts as a particle enters the detection zone of the beam. When the particle is totally within the beam, the scattering will be essentially constant, in that the ratio of the outputs of all detectors will be constant. While the particle may change orientation slightly while in the beam such change is presumed to be small, as the time in the beam may be on the order of 1 millisecond and water has considerable viscosity. The intensity of the beam changes across its thickness in a Gaussian manner, and the beam is presumed to continue from the maximum intensity at the center to where the intensity has dropped to $1/e^2$, or about 1/10th of maximum intensity (e is the base of natural logarithms). However, since the photodetectors detect light only from the detect zone, any low intensity light of the beam outside the detect zone has little or no effect. Applicant prefers, for analysis, to use the maximum output of each detector during an event, when a particle passes through the beam, although it would be possible to use the integral of each detector output or the average of each detector output, or other representation of the detector outputs during an event (the passage of a particle through the detect zone).

Figure 4:
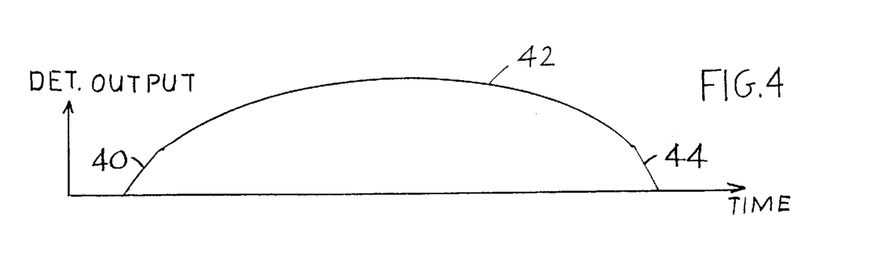
FIG. 4 is a graph showing variation in the output of one the detectors of FIG. 1 with time, as a particle passes through the beam.

FIG. 4 shows the combined time vs. amplitude output of all detectors, showing a ramp rise at 40 as the particle enters the laser beam, an output at 42 as the particle moves through the beam and the light intensity changes, and a ramp fall at 44 as the particle moves out of the beam. In FIG. 2, the particle has a diameter D which is one-tenth the thickness T of the laser beam, so the length of the dwell time 42 in FIG. 4 is 9 times the length of the rise 40 and the fall 44. While the fluid can flow along the direction of arrow 12 (FIG. 2) at a variety of velocities, a velocity such as 8 centimeters per second is one velocity used by applicant that is readily established as by gravity flow of liquid. With such a velocity, it takes 1.5 milliseconds for the particle P to move through the beam of thickness T of 100 microns or 0.1 mm.

The width W of the beam is much greater than the thickness T. In one example, the width W is 1.5 mm, which is fifteen times the thickness T of 0.1 mm. The large width W results in a short period between successive particles passing through the beam 16. In one example, there are 500 particles per milliliter (1 cubic centimeter) for particles of 1 to 20 microns diameter. Particles greater than twenty microns diameter have been filtered out. The laser has a wavelength of about 0.6 microns, and is assumed to detect only particles of at least one to two wavelength. Assuming the fluid contains 500 particles per milliliter, a flow rate of 8 centimeters per second, a detection zone width (equal to the beam width W) and length parallel to the beam each equal to 1.5 mm, and a detection zone thickness T of 0.1 mm, one would expect about 100 particles per second to pass through the detect zone of the laser beam. Each particle takes about 1.5 millisecond to pass through the beam, so one would expect about 10 milliseconds between detections and perhaps only one detection in 10 involving two particles passing at the same time through the detection zone of the laser beam.

If the density of particles is 5000 particles per milliliter, in the above example, then about one-third of the time there will be only one particle traversing the beam, about one-third of the time more than one particle will lie in the beam, and one-third of the time no particle will lie in the beam. The time when only one particle lies in the beam during the beam traverse of that particle, is the only time when useful data is generated. The 5000 particles per milliliter density is about the maximum particle density, in the above example, that is useful; this density in the example, generates data at the maximum rate.

To avoid too many detections of two particles in the beam, applicant can reduce the width of the laser beam and/or thickness. This results in fewer particles passing through the laser beam detection zone, thereby reducing the number of "doubles", which is when two particles lie in the beam at the same time. Care must be taken that the thickness of the beam is greater than the diameter of substantially every particle, almost everywhere along the width of the beam. This assures that almost every particle will lie completely within the beam at some time during its transit of the beam, and assure that the particle lies in the beam long enough for the detectors to accurately detect the amount of scattered light. The ratio of width to thickness of the laser beam can be adjusted by lenses through which the laser beam passes.

Applicant prefers to have a laser beam width W which is about 16 times the thickness T. Applicant prefers that the width be a plurality of times the thickness, preferably more than 5 times the thickness, and more preferably more than 8 times the thickness. Applicant finds that horizontal expansion of the original laser beam results in a cross-sectional shape such as shown in FIG. 2, with a convex top and bottom. The radius of curvature of the top and bottom is on the order of magnitude of 100 times the maximum thickness Tm of the beam (i.e., 10 to 1000 time Tm). As mentioned above, the intensity of the beam is greatest at the center of its height, or thickness, and decreases at locations closer to the top and bottom. It is also noted that the dimensions of the laser beam cross-section given above are for the beam location at the detection zone. The width and thickness of the beam increase at greater distances from the laser, although the cross-sections remain geometrically similar.

Figures 5, 6, 7:
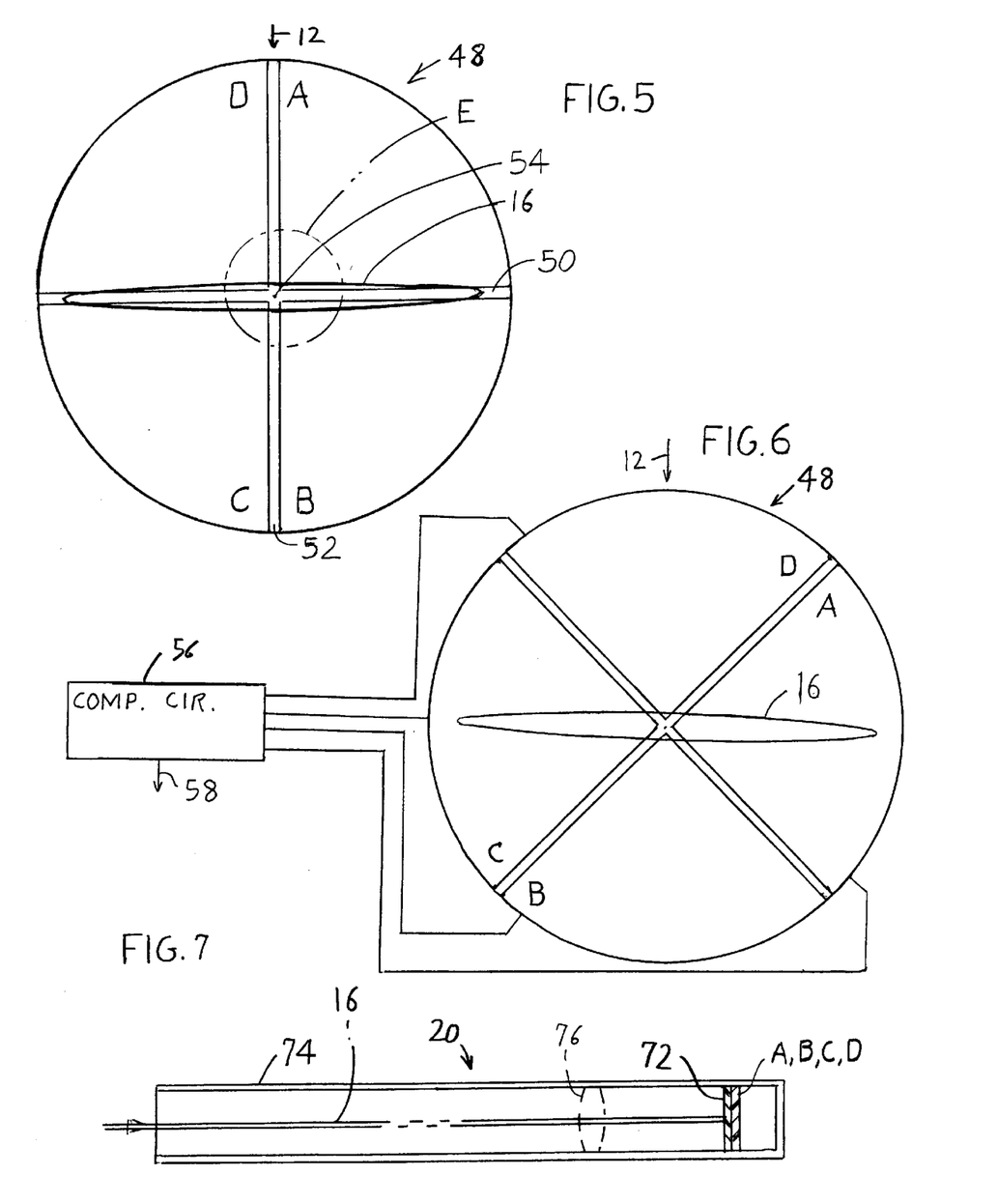
FIG. 5 is a front elevation view of a quadrant detector of the prior art, and showing, in phantom lines, how a beam of round cross section has been detected in the prior art, and showing, in solid lines, one possible way of detecting the laser beam of FIG. 2.
FIG. 6 is a front elevation view of the quadrant detector of FIG. 5, showing a preferred orientation of the quadrant detector for detecting the beam of FIG. 2.
FIG. 7 is a sectional view of a dump of the apparatus of FIG. 1, and which contains the quadrant detector of FIG. 6.

Another problem to be overcome in setting up and checking the apparatus, is to assure that the laser beam passes precisely along the desired path. This assures that substantially all of the laser beam passes through the detect zone 22 shown in FIG. 1, at which all of the photodetectors 30 are aimed, and that substantially all of the detect zone is occupied by the laser beam. FIG. 5 shows a prior art quadrant detector 48 which includes four light detectors, or photodetectors, or photo cells, labeled A, B, C and D that lie on opposite sides of inactive thin strip, or line areas 50, 52. A line area is an area having a width that is small fraction (less than 5%) of its length. The figure shows a prior art laser beam E of round cross-section which is poorly aligned, in that the center of the laser beam does not lie on the centerpoint 54 where the strip areas 50, 52 cross. The outputs of the four photodetectors or photocells A–D are compared. Only if the output of cell A equals the output of cell C, and the output of cell B equals the output of cell D, is the beam centered on the center point 54. FIG. 5 also shows how applicant's elongated laser beam could be centered using the quadrant detector 48. Applicant's beam is centered only if the outputs of A and C are equal and the outputs of B and D are equal. However, applicant notes that in the centered position of the beam 16, much of the beam lies in the inactive strip areas 50, 52 where the beam is not detected. The strip areas 50, 52 must be made very small (e.g. less than 0.05 mm thickness for a beam of 0.1 mm thickness) or the laser beam must be magnified (e.g. by lens 76 in FIG. 7).

FIG. 6 shows the quadrant detector 48 turned 450 from the horizontal orientation of the beam 16, and with the beam centered. It can be seen that most of the beam falls on the detectors. As in FIG. 5, beam centering requires that the output of A equals that of C, and the output of B equals that of D. Only the center of the beam falls on detectors B and D so centering is more consistent than in FIG. 5. Rotation of the beam by about 45° (30 to 60) from the orientation of FIG. 5 is desirable, but rotation by 45° is preferred for simplicity. FIG. 6 shows a comparison circuit 56 that compares the outputs of pairs at cells and that generates an output 58 representing the differences.

The laser source 14 of FIG. 1 is held on a mount that permits adjustment of the laser beam. The mount permits pivoting about two perpendicular axes 60, 62 to change the direction of the beam (pivot up and down or side to side), and permits translation (movement without requiring pivoting) of the laser along each axis 60, 62 to shift the position of the beam (shift up and down or side to side). Such a mount can include motors that drive lead screws to slightly pivot or shift the laser. The computer compares the outputs of the four photocells A–D of FIG. 4. If the output of detectors A and C are not equal, the beam position is adjusted until they are equal. A similar comparison is done for the outputs of detectors B and D.

The laser beam is polarized, generally in a vertical direction for the apparatus of FIGS. 1 and 2, and it is important that the direction of polarization be accurately maintained. This can be accomplished by having a vertical polarization filter in front of the photodetectors A, B, C, D of FIG. 6, which is orientated parallel to the direction 12 of fluid flow. The laser (or polarization filter) can be rotated back and forth from its aligned position at 16 in FIG. 6 to be sure that the direction of polarization of the laser beam is parallel to the direction of polarization of the polarization filter in front of the four photodetectors A–D. The rotational position of maximum output is the position of alignment of the polarizations of the laser beam and the polarization filter.

It is also desirable to monitor the output of the laser to determine whether the output has increased or decreased from a nominal value, to either take this into account in evaluating the outputs of the photodetectors 30 or to change the laser output. This can be accomplished by monitoring the sum of the outputs of the four photocells, or quadrant detector. The output of the quadrant detector can be compared to the output of the internal, or built-in photodiode, in the laser. If the output of the quadrant detector decreases while the output of the built-in photodiode does not (or there is a greater percent decrease in quadrant output than built-in photodiode output), this indicates that the water or equipment is dirty and should be cleaned.

FIG. 7 shows that the dump 20 includes the four photocells A–D, a polarizing filter 72 lying in front of the photocells A–D, and a long narrow tube 74 extending forward of the photocells and preferably also forward of the polarizing filter 72. The tube 74 is used to absorb reflections of a laser beam from the filter 72 and from the photocells A–D. A very high percent of all light from the laser beam, such as 99% or more, reaches the dump 20 where it generates electricity as the output of the cells A–D and generates heat. Only a very small percent is scattered by particles in the fluid, to the photodetectors 30 (FIG. 1) that surround the detect zone. If a significant portion of the laser beam should be reflected by any portion of the dump 20 so that it is reflected to one of the photodetectors 30, then such light could overwhelm and damage the photodetector and in any case could result in erroneous data. The long tube 74 of FIG. 7, which is a plurality of times (preferably at least 4 times) as long as its width, assures that substantially all light which enters the dump is trapped and cannot emerge from it. If the cross-section of the laser beam falling on the photocells A–D is of smaller size than desirable, a magnifying lens 76 can be placed in the tube.

Figure 8:
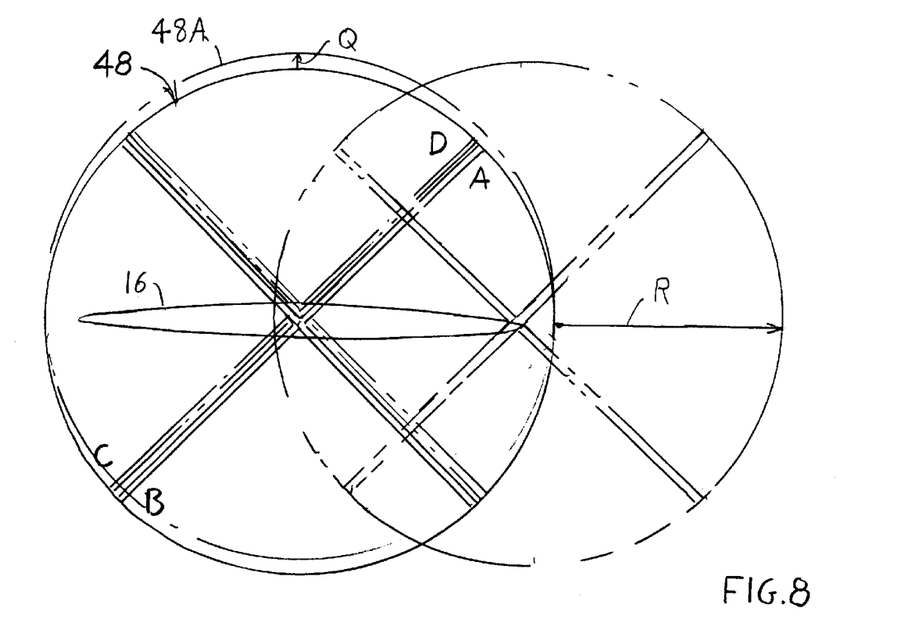
FIG. 8 is a front elevation view showing the quadrant detector of FIG. 6, and indicating directions of movement of the quadrant detector and/or the light beam so as to measure the width and thickness of the beam.

It is desirable to be able to measure the width and thickness of the laser beam at the photocells A–D. FIG. 8 shows one method for detecting the width. The quadrant detector 48 with photocells A–D is moved upward a distance Q from the center position 48 until, at 48A, the photocell D does not detect the laser beam (e.g. the output of D drops to less than 5% of the output of B). The quadrant is then moved downward until photocell D does not detect the beam. The total vertical movement of the beam up and down from the center position equals beam thickness at the photocells. Next, the photocells are moved rightward by a distance R until photocell C does not detect the laser beam and then leftward until photocell A does not detect the beam. The sum of leftward and rightward movement from the center position equals the laser beam width at the photocells. If the laser has been centered on the photocells, it is necessary to move in only one direction such as R, and the beam width is 2R. Instead of moving the photocells, it is possible to pivot an optical deflecting element (e.g. prism or lens) or translate the laser along the axes 60, 61 in FIG. 1.

Figure 9:
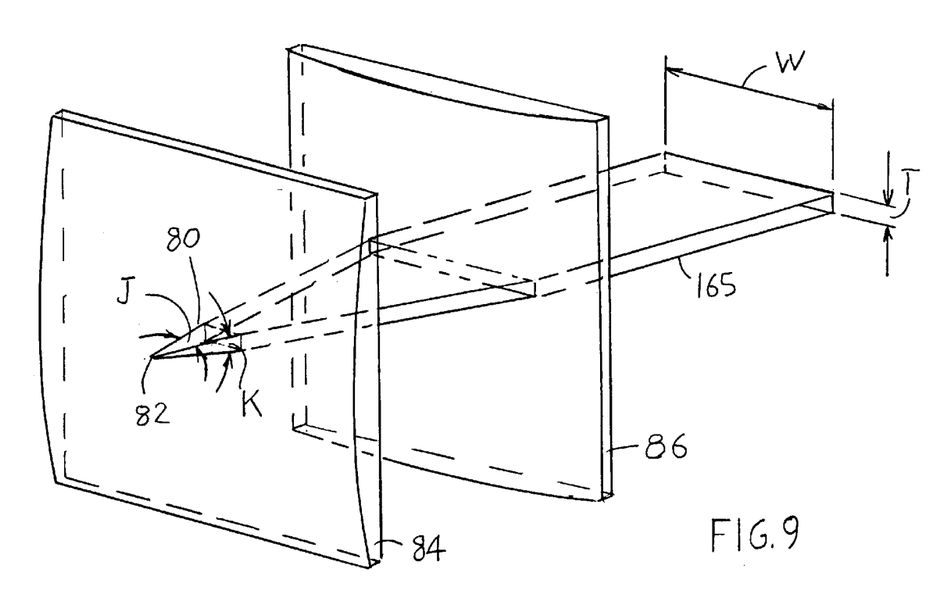
FIG. 9 is an isometric view showing a manner in which applicant can generate the laser beam having the cross section of FIG. 2.

It is noted that laser beams from gas lasers are round, and can be collimated to produce a round beam of constant diameter. However, laser beams from solid state lasers such as diode lasers commonly expand differently in different directions. FIG. 9 shows a simplification of the output 80 from an emitting portion 82 of a diode laser, the emitting portion being a fraction of the eventual beam thickness T. The solid state laser output expands at an angle J of 30° in one direction and at an angle K of 7.5° in a perpendicular direction (i.e. about a perpendicular axis). Applicant places a convex cylindrical collimating lens 84 where the beam thickness has expanded to about 0.1 mm, and places another convex cylindrical collimating lens 86 where the beam width has expanded to 1.5 mm. This results in a beam 165 having a thickness T of about 0.1 mm and a width of about 1.5 mm, resulting in a beam having a width to thickness ratio of 15 to 1. In the prior art, most equipment was designed for use with a gas laser which produces a beam of round cross-section, and when solid state lasers became available optics were used that produced a collimated beam of roughly round cross-section. The primarily cylindrical lenses 84, 86 may not collimate the beam, but reduce the expansion angle to less than half the original angles J, K. The lens may substantially collimate the beam (expansion or contraction angle of less than 5°).

While terms such as "horizontal" and "vertical" have been used to help describe the invention as it is illustrated, it should be noted that the invention can be used in any orientation with respect to the Earth.

Thus, the invention provides an apparatus and method for use in detecting microscopic particles by the detection of light scattered by a particle passing through a detect zone along a beam, which reduces the occurrence of two or more particles simultaneously lying in the detect zone while maximizing the number of particles passing through the zone in a given time period, which enables orientation of the beam, which enables measurement of the width and thickness of the beam, and which easily generates the beam. The width of the beam is preferably a plurality of times as great as the average thickness of the beam. The orientation of the beam is detected by a quadrant detector which is oriented about 45° from a prior art orientation. The width and thickness of the beam can be checked by an activator that moves the quadrant detector and/or the beam. The beam with a large width to thickness ratio, is generated by a pair of primarily cylindrical lenses placed in front of a semiconductor laser, with the spacing of the lenses chosen to produce the desired width to thickness ratio.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for use in identifying particles that are present in fluid to be analyzed, wherein the fluid moves largely in a predetermined fluid movement direction along a fluid oath that contains said particles to be identified, which includes a beam generator that generates a beam of light, and a plurality of detectors that each detects light scattered from a detection zone lying along the beam when a particle passes through the detection zone, wherein:

said beam generator is constructed to generate a light beam moving along a predetermined beam direction and having a beam width and a beam thickness as measured in directions that are perpendicular to each other and that are each perpendicular to said beam direction;

said beam width is a plurality of times as great as said beam thickness, and said beam thickness extends primarily parallel to said fluid movement direction while said beam width extends primarily perpendicular to said fluid movement direction, whereby to minimize the time for passage of each particle through said beam and maximize the number of particles passing through said beam per time period;

said fluid path has a oath width greater than said beam width, and said beam is positioned so the entire beam width lies in said path, wherein said particles can pass through any location along the width of the beam.

2. The apparatus described in claim 1 wherein:

said beam width is more than five times said beam thickness;

Said beam thickness is an average thickness of said beam along a cross-section of the beam at said detection zone, with the beam thickness at any location across the width of the beam at the detection zone ending where the intensity of the light drops to less than $1/10$th the maximum intensity of light at the center of the beam thickness thereat.

3. The apparatus described in claim 2 wherein:

said beam width is more than eight times said beam thickness at said detection zone.

4. A method for identifying particle that are present in fluid to be analyzed wherein the fluid moves largely along in a predetermined fluid movement direction along a fluid path that contains said particles to be analyzed which includes generating a beam of light that moves along a light path and detecting light scattered from a particle passing through a detection zone that lies along said light path of the beam, wherein:

said step of generating a beam of light includes producing a beam that has a cross-section at said detection zone wherein said cross-section has a width in a width direction that is perpendicular to said light path and that is primarily perpendicular to said predetermined fluid movement direction, and wherein said cross-section has a thickness in a direction perpendicular to said width and to said light path;

said step of producing a beam includes producing a beam whose width is more than five times its thickness at said detect tone;

said fluid path has a width that is greater than said beam width, and the entire width of the beam passes through said fluid path.

5. The method described in claim 4 wherein:

said step of producing including producing a beam whose width is at least eight times its thickness at said detect zone.

6. Apparatus for use in identifying particles that are present in fluid, which includes a beam generator that generates a beam of light that is generated along a beam path, wherein:

said beam of light has a beam width and a beam thickness, in directions that are perpendicular to each other and that are each perpendicular to said beam path, said beam width being a plurality at times as great as said beam thickness; and including:

a quadrant detector that includes four photodetectors lying in each of the four quadrants formed by two perpendicular line areas, said quadrant detector lying along said beam path to be illuminated by said beam during a test;

a difference circuit that generates a signal representing the difference in outputs of opposite ones of said photodetectors;

said quadrant detector being oriented with each of said perpendicular lines extending about 45° to the directions of said beam width and to same beam thickness.

7. The apparatus described in claim 6 wherein:

said quadrant detector has a center where said perpendicular line areas cross; and including:

activator means for moving said quadrant detector relative to said beam, in a direction primarily parallel to said beam width, to thereby enable a determination of the width of said beam.

8. The apparatus described in claim 6 wherein:
said quadrant detector has a center where said perpendicular line areas cross; and including:
activator means for moving said quadrant detector relative to said beam, in a direction primarily parallel to said beam thickness to thereby determine whether or not said beam thickness is centered on said quadrant detector.

9. Apparatus for use in identifying particles that are present in fluid, which includes a beam generator that generates a beam of light that is directed along a beam path, wherein:
said beam of light has a beam width and a beam thickness, in directions that are perpendicular to each other and that are each perpendicular to said beam path, said beam width being greater than said beam thickness;
a quadrant detector that includes four photodetectors lying in each of the four quadrants-formed by two perpendicular line areas, said quadrant detector lying along said beam path to be illuminated by said beam during a test;
a difference circuit that generates a signal representing the difference in outputs of opposite ones of said photodetectors;
activator means for moving said quadrant detector relative to said beam, in a direction primarily parallel to said beam width, to thereby enable a determination of a cross-sectional dimension of said beam.

10. Apparatus for use in identifying particles that are present in fluid, which includes a laser that generates a beam of light that is directed along a beam path, wherein:
said beam of light has a beam width and beam thickness, in directions that are perpendicular to each other and that are each perpendicular to said beam path;
a photocell positioned along said beam of light;
a circuit connected to said photocell that indicates the output of said photocell;
a polarizing filter positioned along said beam of light;
means for rotating said photocell relative to said laser.

11. Apparatus for use in identifying particles that are present in fluid to be analyzed, wherein the fluid moves largely along a predetermined fluid movement direction, which includes a beam generator that generates a beam of light, and a plurality of detectors that each detects light scattered from a detection zone lying along the beam when a particle passes through the detection zone, wherein:
said beam generator is constructed to generate a light beam moving along a predetermined beam direction and having a beam width and a beam thickness as measured in directions that are perpendicular to each other and that are each perpendicular to said beam direction;
said beam width is a plurality of times as great as said beam thickness and said beam thickness extends primarily parallel to said fluid movement direction while said beam width extends primarily perpendicular to said fluid movement direction, whereby to minimize the time for passage of each particle through said beam and maximize the number of particles passing through said beam per time period;
said beam has upper and lower surfaces separated by said beam thickness, said upper and lower surfaces each being convex with a radius of curvature on the order of magnitude of 100 times the beam thickness.

12. Apparatus for use in identifying particles that are present in fluid to be analyzed, wherein the fluid moves largely along a predetermined fluid movement direction, which includes a beam generator that generates a beam of light, and a plurality of detectors that each detects light scattered from a detection zone lying along the beam when a particle passes through the detection zone, wherein:
said beam generator is constructed to generate a light beam moving along a predetermined beam direction and having a beam width and a beam thickness as measured in directions that re perpendicular to each other and that are each perpendicular to said fluid movement direction, whereby to minimize the time for passage of each particle through said beam and maximize the number of particles passing through said beam per time period;
a dump positioned along the path of said light beam, said dump having at least one photocell for detecting light;
a circuit for measuring the output of said at least one photocell;
a polarizing filter lying along the path of said light beam between said beam generator and said photocell;
said beam having an axis extending along said beam path, and of said beam generator and said filter, means for rotating one of them relative to the other about said axis.

13. Apparatus for use in identifying particles that are present in fluid to be analyzed, wherein the fluid moves largely along a predetermined fluid movement direction, which includes a beam generator that generates a beam of light, and a plurality of detectors that each detects light scattered from a detection zone lying along the beam when a particle passes through the detection zone, wherein:
said beam generator is constructed to generate a light beam moving along a predetermined beam direction and having a beam width and a beam thickness as measured in directions that are perpendicular to each other and that are each perpendicular to said beam direction;
said beam width is a plurality of times as great as said beam thickness, and said beam thickness extends primarily parallel to said fluid movement direction, whereby to minimize the time for passage of each particle through said beam and maximize the number of particles passing though per beam per time period;
a quadrant detector that includes four photocells each lying in one of the four quadrants formed by two perpendicular line areas where light is not detected by one of the four photocells, said quadrant detector lying along said beam path to be illuminated by said beam during a test;
a difference circuit that generates a signal representing the difference in outputs of opposite ones of said photocells;
said quadrant detector being oriented so said perpendicular line areas are each inclined by about 45° from the horizontal when said beam width is horizontal.

14. The apparatus described in claim 13 including:
activator means for moving said quadrant detector relative to said bem, in a direction primarily parallel to said beam width, to thereby enable measurement of beam width.

15. A method for identifying particles that are present in fluid to be analyzed wherein the fluid moves largely along a predetermined fluid movement direction, which includes generating a beam of light that moves along a light path and detecting light scattered from a particle passing through a detection zone that lies along said light path of the beam, wherein:

said step of generating a beam of light includes producing a beam that has a cross-section at said detection zone wherein said cross-section has a width in width direction that is perpendicular to said light and that is primarily perpendicular to said predetermined fluid movement direction, and wherein said cross-section has a thickness in a direction perpendicular to said width and to said light path;

said step of producing a beam includes producing a beam whose width is more than five times its thickness at said detect zone;

placing a quadrant detector that has four photocells lying in different ones of four quadrants separated by two perpendicular line areas, along said light path in a test;

detecting differences in the outputs of a pair of diagonally-opposite ones of said photocells to determine the accuracy of centering of said beam on said quadrant detector;

said step of placing including orienting said lines areas so they each extend about 45° to the horizontal when said width direction of said beam is horizontal.

* * * * *

UNITED STATES PATENT AND TRADEMARK OFFICE
CERTIFICATE OF CORRECTION

PATENT NO. : 6,628,386 B2  Page 1 of 1
DATED : September 30, 2003
INVENTOR(S) : Clay Davis, Donald Mead and Gregory Quist It is certified that error appears in the above-identified patent and that said Letters Patent is hereby corrected as shown below:

<u>Column 7,</u>
Line 64, change "oath" to -- path --

Signed and Sealed this

Eleventh Day of November, 2003

JAMES E. ROGAN
*Director of the United States Patent and Trademark Office*